United States Patent
Frisby et al.

(10) Patent No.: US 9,588,083 B2
(45) Date of Patent: Mar. 7, 2017

(54) DETERMINING THE PHASE COMPOSITIONS OF A MULTIPHASE FLUID FLOW

(71) Applicant: Spirax-Sarco Limited, Gloucestershire (GB)

(72) Inventors: Ben Frisby, Gloucestershire (GB); Nashtara Islam, Gloucestershire (GB); Peter Usher, Gloucestershire (GB); Mitchell Kane, Gloucestershire (GB)

(73) Assignee: Spirax-Sarco Limited, Gloucestershire (GB)

( * ) Notice: Subject to any disclaimer, the term of this patent is extended or adjusted under 35 U.S.C. 154(b) by 137 days.

(21) Appl. No.: 14/026,215

(22) Filed: Sep. 13, 2013

(65) Prior Publication Data

US 2014/0069168 A1 Mar. 13, 2014

(30) Foreign Application Priority Data

Sep. 13, 2012 (GB) .................................. 1216390.3

(51) Int. Cl.
*G01N 29/02* (2006.01)
*G01N 29/14* (2006.01)
(Continued)

(52) U.S. Cl.
CPC ............. *G01N 29/02* (2013.01); *G01N 29/14* (2013.01); *G01N 29/222* (2013.01); *G01N 29/42* (2013.01);
(Continued)

(58) Field of Classification Search
CPC .... G01N 29/02; G01N 29/024; G01N 29/036; G01N 29/14; G01N 29/4427;
(Continued)

(56) References Cited

U.S. PATENT DOCUMENTS

| 3,854,323 A | 12/1974 | Hearn et al. |
| 4,646,273 A | 2/1987 | Carlson et al. |

(Continued)

FOREIGN PATENT DOCUMENTS

| EP | 1174713 | 1/2002 |
| EP | 1481223 | 9/2003 |

(Continued)

OTHER PUBLICATIONS

European Patent Office, "European Search Report," issued in connection with European application serial No. 13183340.2, issued Dec. 20, 2013, 5 pages.

(Continued)

*Primary Examiner* — Lisa Caputo
*Assistant Examiner* — Tran M Tran
(74) *Attorney, Agent, or Firm* — Banner & Witcoff, Ltd.

(57) ABSTRACT

A method of determining the phase compositions of a multiphase fluid flow in a fluid line, including obtaining a vibration signal from the fluid flow using a vibration sensor comprising a target disposed in the fluid flow which vibrates in response to fluid flow in the fluid line. The vibration signal is analyzed to determine a first energy parameter which is related to the energy of the vibration signal within a first frequency band, and a second energy parameter which is related to the energy of the vibration signal within a second frequency band; and a phase composition parameter, such as a dryness parameter, relating to the phase compositions of the fluid flow is determined using the first and second energy parameters. An apparatus for determining the phase compositions of a multiphase fluid flow in a fluid line.

15 Claims, 4 Drawing Sheets

(51) Int. Cl.
*G01N 29/44* (2006.01)
*G01N 29/46* (2006.01)
*G01N 29/22* (2006.01)
*G01N 29/42* (2006.01)

(52) U.S. Cl.
CPC ......... *G01N 29/4427* (2013.01); *G01N 29/46* (2013.01); *G01N 2291/02425* (2013.01); *G01N 2291/02845* (2013.01)

(58) Field of Classification Search
CPC ...... G01N 29/46; G01N 29/42; G01N 29/222; G01N 2291/02425; G01N 2291/02433; G01N 2291/02845
See application file for complete search history.

(56) References Cited

U.S. PATENT DOCUMENTS

| | | | | |
|---|---|---|---|---|
| 4,832,503 A | * | 5/1989 | Dowling et al. | 374/42 |
| 5,035,146 A | | 7/1991 | Chien | |
| 5,415,048 A | * | 5/1995 | Diatschenko et al. | 73/861.04 |
| 5,524,475 A | * | 6/1996 | Kolpak et al. | 73/19.03 |
| 9,046,401 B2 | * | 6/2015 | Henry et al. | |
| 2003/0235263 A1 | | 12/2003 | Rajendran et al. | |
| 2014/0069168 A1 | * | 3/2014 | Frisby et al. | 73/24.06 |

FOREIGN PATENT DOCUMENTS

| | | |
|---|---|---|
| JP | 2012156277 A | 8/2012 |
| WO | 2010094809 | 8/2010 |

OTHER PUBLICATIONS

Intellectual Property Office of Great Britain, "Seach Report," issued in connection with application serial No. GB1216390.3, issued Nov. 28, 2012, 2 pages.

Jul. 19, 2016—(JP) Office Action—App. No. 2013-190997—3 pages.

* cited by examiner

DETERMINING THE PHASE COMPOSITIONS OF A MULTIPHASE FLUID FLOW

CROSS-REFERENCE TO RELATED APPLICATIONS

The present application claims priority to GB 1216390.3 filed on 13 Sep. 2012, which is hereby incorporated by reference in its entirety for any and all purposes.

FIELD

The aspects of the invention relates to a method and apparatus for determining the phase compositions of a multiphase fluid flow, in particular, although not exclusively, to a method and apparatus for determining the dryness of wet steam.

BACKGROUND

The use of steam as a heating medium in industrial processes is very widespread. Most process and heating steam systems use saturated wet steam which is a two-phase fluid comprising vapour as a first phase and condensate as a second phase.

It is often necessary to know the dryness, or quality, of the wet steam. Steam quality is the percentage of the mass of the fluid that is vapour, and therefore saturated steam has a steam quality of 100% and saturated liquid has a steam quality of 0%.

Some industrial processes have particular requirements regarding steam quality. For example, in sterilisation systems the steam quality must be between 95%-100%. This is set-out by standard BS EN 285 which specifies the requirements and relevant tests for large steam sterilisers primarily used in health care. Currently, steam quality is typically measured using throttling calorimetry. An example of an apparatus and method for measuring steam quality using a throttling calorimeter is disclosed in GB 1906 12,615. Whilst throttling calorimetry can be used to successfully determine the quality of steam, it is a time-consuming process and the apparatus is relatively complicated.

It is therefore desirable to provide an improved method and apparatus for determining the phase compositions of a multiphase fluid flow.

SUMMARY

Various aspects of the invention are defined in the attached independent claims to which reference should now be made. Further, certain features may be found in the sub-claims appended thereto.

In one broad aspect the invention concerns a method and apparatus for determining the phase compositions (which may be the dryness) of a multiphase fluid flow, such as wet steam, from the characteristics of one or more vibration signals obtained from the fluid flow.

According to an aspect of the invention there is provided a method of determining the phase compositions (which may be the dryness) of a multiphase fluid flow in a fluid line, comprising: obtaining a vibration signal from the fluid flow using a vibration sensor comprising a target disposed in the fluid flow which vibrates in response to fluid flow in the fluid line; analysing the vibration signal to determine a first energy parameter which is related to the energy of the vibration signal within a first frequency band, and a second energy parameter which is related to the energy of the vibration signal within a second frequency band; and determining a phase composition parameter (which may be a dryness parameter) relating to the phase compositions (which may be the dryness) of the fluid flow using the first and second energy parameters. The phase composition parameter may be determined empirically from the first and second energy parameters.

The target may be a diaphragm. The vibration sensor may further comprise an electrical converter for converting the vibration of the target into a vibration signal. The electrical converter may comprise a piezoelectric transducer. The first and/or second frequency band may be a single frequency or a range of frequencies. The first and/or second energy parameter may be any suitable parameter that can be derived or determined from the vibration signal and which can be related together to arrive at the phase compositions/dryness of the fluid flow.

In some embodiments, but not necessarily in all embodiments, the target may vibrate in response to fluid flow impact on the target. The target may be configured to resonate at one or more resonant frequencies. The vibration signal may be analysed to determine a first and/or a second energy parameter which is the amplitude of one or more resonant frequencies of the vibration signal.

The fluid flow may be mixed upstream of the vibration sensor. This may help to ensure that the fluid flowing in the line is substantially uniform.

The vibration sensor may measure the vibration signal in the time domain. Analysing the vibration signal may include transforming the vibration signal from the time domain to the frequency domain. The vibration signal may be transformed from the time domain to the frequency domain using a fast Fourier transform (FFT).

The first energy parameter may be dependent on the flow velocity. This may mean that the first energy parameter may change in response to a change in the flow velocity. The second energy parameter may be dependent on the phase compositions of the fluid flow and the flow velocity. In other words, the second energy parameter may change in response to a change in either the flow velocity or the phase compositions of the fluid flow.

The first energy parameter may be the total energy of the vibration signal within the first frequency band and the second energy parameter may be the total energy of the vibration signal within the second frequency band. The total energy may be determined by summing the amplitudes of all of the frequencies with the particular frequency band. The first energy parameter may be the amplitude of the peak frequency within the first frequency band and the second energy parameter may be the amplitude of the peak frequency within the second frequency band. In other embodiments, the first and/or second energy parameter may be the average amplitude of all frequencies within the particular band, or may be any other suitable value capable of characterising the energy of the vibration signal within the particular frequency band.

The first frequency band and/or the second frequency band may be predetermined or fixed for a particular installation. Analysing the vibration signal may include defining the first frequency band about a first peak frequency and/or defining the second frequency band about a second peak frequency. The method may include detecting a first and/or a second peak frequency. The first frequency band may contain a first peak frequency and/or the second frequency band may contain a second peak frequency. The first frequency band may be at a lower frequency than the second frequency band.

The method may further comprise determining a temperature parameter relating to the temperature of the fluid flow. The phase composition and/or dryness parameter may be determined by using a first energy parameter, a second energy parameter and the temperature parameter. The temperature parameter may be an actual temperature, or may be some other parameter that is related to temperature, for example pressure.

Determining a phase composition and/or a dryness parameter may comprise accessing a database containing data correlating first energy parameters and second energy parameters with phase composition parameters. If the multiphase fluid is wet steam, the dryness parameter may be expressed as a percentage where 100% is saturated vapour and where 0% is saturated liquid. The dryness parameter may be known as "steam quality".

The method may further comprise outputting the phase composition and/or dryness parameter. Outputting the phase composition and/or dryness parameter may comprise displaying and/or transmitting the phase composition and/or dryness parameter. The phase composition and/or dryness parameter may be transmitted wirelessly.

The fluid flow may be a steam flow, such as wet steam. The dryness parameter may be known as the "vapour quality".

According to another aspect of the aspects of the invention there is provided an apparatus for determining the phase compositions (which may be the dryness) of a multiphase fluid flow flowing in a fluid line, comprising: a vibration sensor comprising a target arranged to be disposed in the fluid flow which vibrates in response to fluid flow in the fluid line for obtaining a vibration signal from the fluid flow; a vibration signal analysis unit for analysing the vibration signal to determine a first energy parameter which is related to the energy of the vibration signal within a first frequency band, and a second energy parameter which is related to the energy of the vibration signal within a second frequency band; and a phase composition determining unit (which may be a dryness determining unit) for determining a phase composition parameter (which may be a dryness parameter) relating to the phase compositions (which may be the dryness) of the fluid flow using the first and second energy parameters.

The apparatus may further comprise a fluid mixer for mixing the fluid flow upstream of the vibration sensor.

The vibration sensor may be arranged to measure the vibration signal in the time domain. The vibration signal analysis unit may be arranged to transform the vibration signal from the time domain to the frequency domain. The vibration signal analysis unit may be arranged to transform the vibration signal from the time domain to the frequency domain using a fast Fourier transform (FFT).

The first energy parameter may be dependent on the flow velocity. The second energy parameter may be dependent on the phase compositions of the fluid flow and the flow velocity. The first energy parameter may be the total energy of the vibration signal within the first frequency band and the second energy parameter may be the total energy of the vibration signal within the second frequency band. The first energy parameter may be the amplitude of the peak frequency within the first frequency band and the second energy parameter may be the amplitude of the peak frequency within the second frequency band. The first frequency band may be predetermined and the second frequency band may be predetermined. The vibration signal analysis unit may be arranged to define the first frequency band about a first peak frequency and the vibration signal analysis unit may be arranged to define the second frequency band about a second peak frequency. The first frequency band may contain a first peak frequency and the second frequency band may contain a second peak frequency. The first frequency band may be at a lower frequency than the second frequency band.

The apparatus may further comprise a database containing data correlating first energy parameters and second energy parameters with phase composition and/or dryness parameters. The phase composition and/or dryness determining unit may be arranged to access the database so as to determine a phase composition and/or dryness parameter relating to the phase compositions and/or dryness of the fluid flow.

The apparatus may further comprise an outputting unit for outputting the phase composition and/or dryness parameter. The outputting unit may comprise a display for displaying the phase composition and/or dryness parameter and/or a transmitter for transmitting the phase composition and/or dryness parameter.

The apparatus may be arranged to determine the phase compositions and/or the dryness of a steam flow.

The apparatus may further comprise a length of pipe having connectors at either end, wherein the target is disposed within the pipe. A fluid mixer may be disposed within the pipe in front of the target. The distance between the connectors may be in accordance within a predetermined standard.

The target may be a diaphragm. In some embodiments the target may be arranged to resonate in response to fluid flow impact. The vibration sensor may further comprise an electrical converter for converting the vibration of the target into a vibration signal. The electrical converter may comprise a piezoelectric transducer.

The aspects of the invention also concerns a steam system comprising an apparatus in accordance with any statement herein.

The aspects of the invention may comprise any combination of the features and/or limitations referred to herein, except combinations of such features as are mutually exclusive.

BRIEF DESCRIPTION OF THE DRAWINGS

Embodiments of the aspects of the invention will now be described, by way of example, with reference to the accompanying drawings, in which.

DETAILED DESCRIPTION

Figure 1:
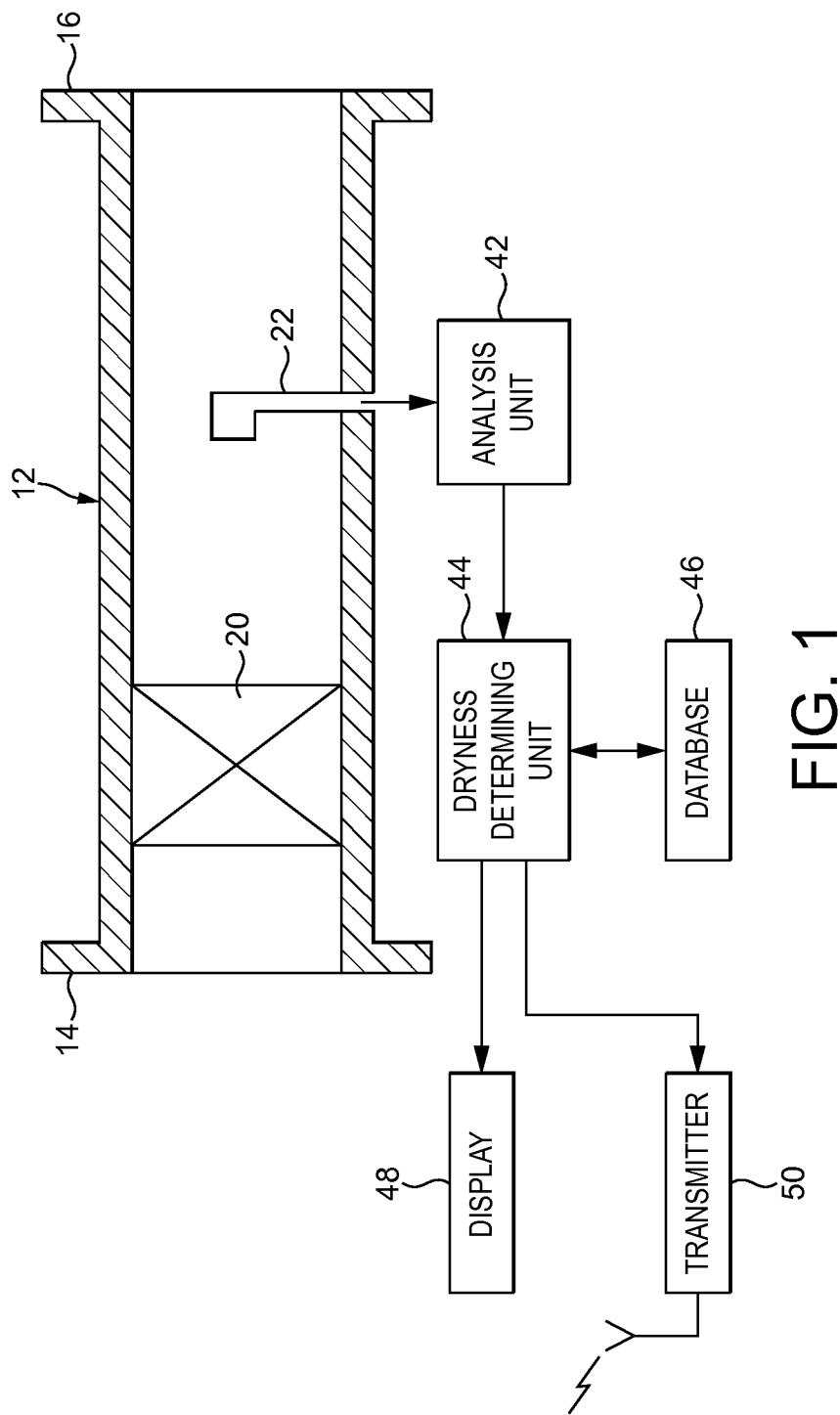
FIG. 1 schematically shows an apparatus for determining the dryness of wet steam flowing in a steam line.

FIG. 1 shows generally at 10 an apparatus for determining the phase compositions of wet steam flowing in a steam line. In this particular embodiment the apparatus 10 is arranged to determine the dryness of the wet steam. The apparatus 10 comprises a length of pipe 12 having connection flanges 14, 16 at either end. The apparatus 10 further comprises a vibration sensor 22 for obtaining a vibration signal from the steam flow and a fluid mixer 20 located upstream for mixing the steam flow.

Figure 2:
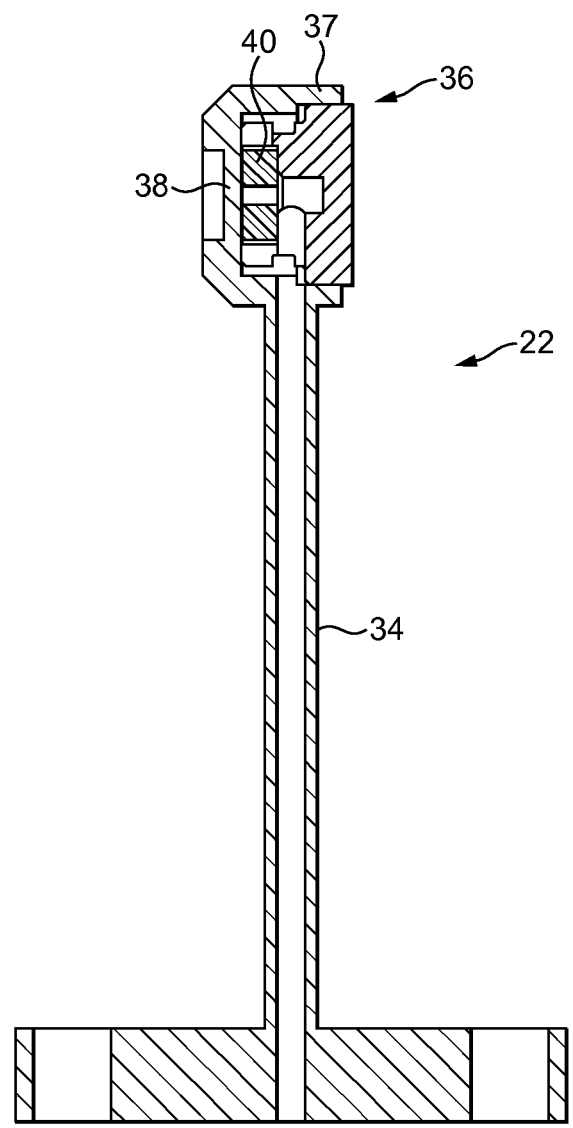
FIG. 2 schematically shows the vibration sensor of FIG. 1.

The vibration sensor 22 is disposed within the pipe 12 downstream of the mixer 20 in the longitudinal direction of the pipe 12 and is shown in more detail in FIG. 2. The vibration sensor 22 comprises a hollow stem 34 that extends into the pipe and a head 36 which is mounted onto the end of the stem 34 and which is aligned with the axis of the pipe. The head 36 comprises a body 37 and a substantially planar target 38 which is in the form of a diaphragm. The target 38 faces the steam flow and lies in a plane perpendicular to the steam flow direction. The target 38 is arranged to vibrate in response to fluid flow within the pipe. A piezoelectric transducer 40 is mounted within the body 37 and is coupled to the target 38 such that vibration of the target 38 in the axial direction is converted into an electrical vibration signal. Signal wires (not shown) are connected to the piezoelectric transducer 40 and pass down the hollow stem 34 to extend to the outside of the pipe 12. The stem 34 and head 36 are manufactured from stainless steel and the diaphragm target 38 is a thin metallic plate.

In this embodiment the apparatus 10 is an integrated unit which can be easily installed in a new steam installation, or can be retrofitted to an existing steam installation, by connecting the flanges 14, 16 to corresponding connection flanges of a steam line such that the pipe 12 forms part of the steam line 12. However, it should be appreciated that in other embodiments the apparatus may be supplied as a series of separate components that must be installed and wired together individually.

In use, the fluid flow within the steam line causes the target 38 to vibrate in the axial direction. If the fluid is wet steam, the fluid flow contains both water droplets and vapour. It has been found by experiment that the electrical vibration signal generated by the target 38 contains characteristics relating primarily to the flow velocity, and characteristics relating to a combination of the dryness of the steam and the flow velocity. Therefore, by using these characteristics, the apparatus 10 can be used to determine the dryness of the steam. In order to ensure that the fluid flow is substantially uniform across the cross-sectional area of the pipe 12, a fluid mixer 20 is disposed in the pipe 12 upstream of the vibration sensor 22. The fluid mixer 20 helps to ensure that no condensate slugs pass under the vibration sensor 22 which would lead to the apparatus determining a steam dryness value higher than the actual value.

Figure 3:
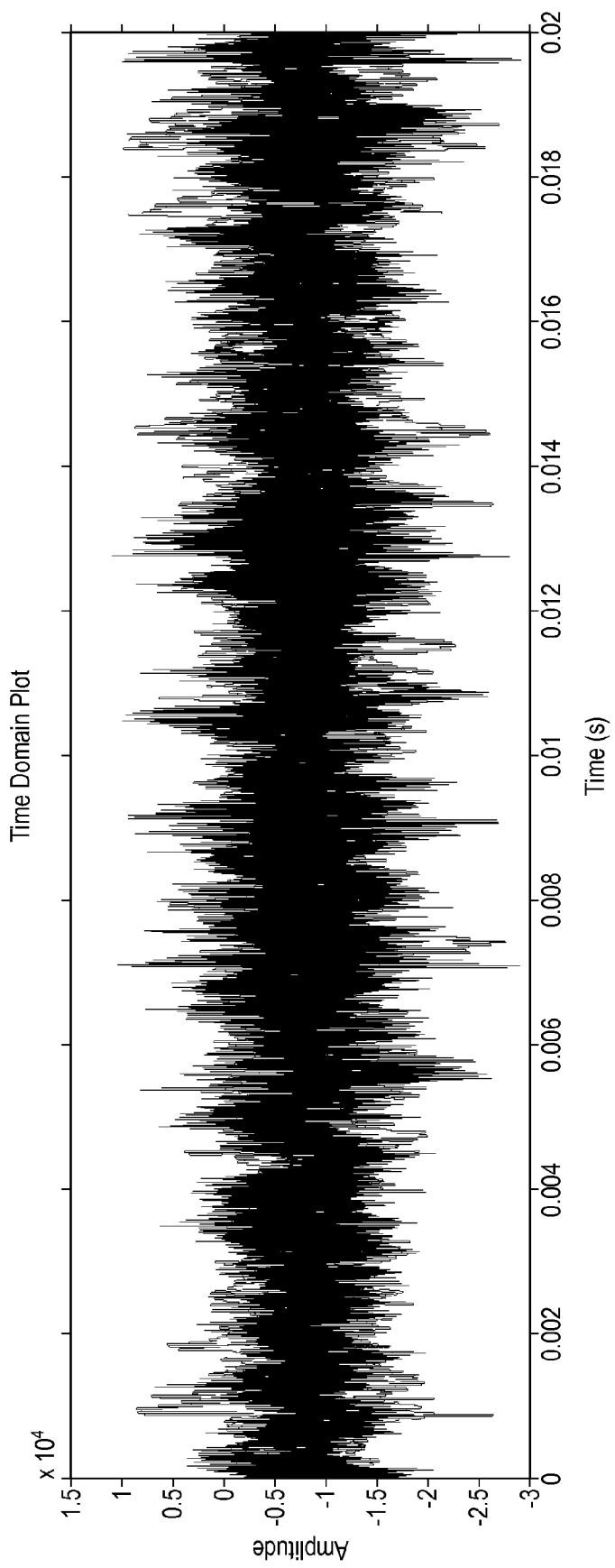
FIG. 3 schematically shows a vibration signal obtained by the vibration sensor in the time domain.
Figure 4:
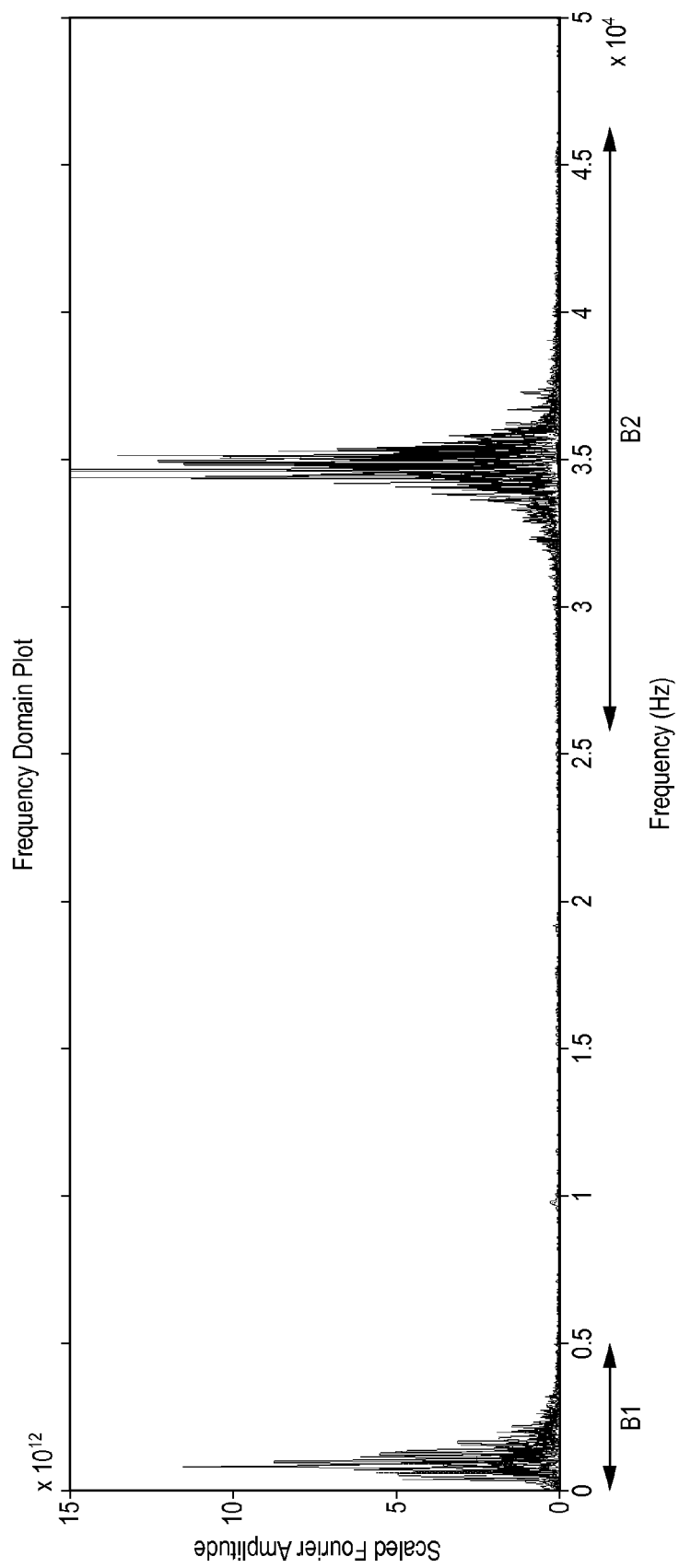
FIG. 4 schematically shows three vibration signals obtained by the vibration sensor in the frequency domain.

The vibration sensor 22 outputs the electrical vibration signal in the time domain and a graphical representation of such a signal is shown in FIG. 3. This vibration signal is output to a vibration signal analysis unit 42. The analysis unit 42 transforms the vibration signal from the time domain to the frequency domain using a fast Fourier transform (FFT) algorithm. A graphical representation of three different vibration signals in the frequency domain is shown in FIG. 4. The three different vibration signals correspond to three different steam flows having different steam dryness values.

As can be seen from FIG. 4, the target 38 vibrates at a first peak frequency and at a second peak frequency that are both substantially the same for all three dryness values. However, the energy of the vibration signals (i.e. the amplitude of the first and second peak frequencies) changes depending on the steam dryness value.

After transforming the vibration signal to the frequency domain, the analysis unit 42 determines the energy of the vibration signal within two predefined frequency bands B1 and B2 that contain the first and second peak frequencies respectively. It has been found by experiment that the vibration signal within the first frequency band B1 is characteristic of the flow velocity only, whereas the vibration signal within the second frequency band B2 (which is at a higher frequency) is characteristic of the phase compositions and the flow velocity. The energy of the vibration signal within the first and second frequency bands B1, B2 is calculated by summing the individual amplitudes of all of the individual frequencies within the particular frequency band B1, B2. In this particular embodiment the first frequency band B1 is 0-4 kHz and the second frequency band B2 is 26-46 kHz. However, it should be appreciated that other frequency bands may be used, as the frequency bands may depend on the particular construction of the vibration sensor and the steam installation as a whole. The energy of the vibration signal within the first frequency band B1 is termed a "first energy parameter E1" and the energy of the vibration signal within the second frequency band B2 is termed a "second energy parameter E2". The first energy parameter E1 is dependent on the flow velocity of the steam flow, and the second energy parameter is dependent on both the phase compositions, or steam dryness value, of the steam flow, and the flow velocity of the steam flow.

In this embodiment the first frequency band B1 and the second frequency band B2 are defined as a range of frequencies, but in other embodiments one or both of the frequency bands could be a single frequency. However, if a FFT is used to transform the vibration signal from the time domain to the frequency domain, if one or more of the frequency bands are defined as a single frequency this will in fact correspond to a range of frequencies defined by the resolution of the FFT. One or both of the frequency bands can be fixed for a particular installation as the peak frequencies are substantially independent of the flow velocity and dryness. However, it may be necessary to change one or both of the frequency bands if the installation changes. In other embodiments, the analysis unit 42 may identify a first peak frequency and/or a second peak frequency, and define the first frequency band B1 about the first peak frequency and/or the second frequency band about the second peak frequency B2.

Although it has been described that the first and second energy parameters E1, E2 are the energies of the vibration signal within first and second frequency bands B1, B2 respectively, the first and/or second energy parameter may be any suitable parameter that is related to the energy of the vibration signal and which can be related with one another, to obtain a value representing the dryness of the steam. In some embodiment the first and second energy parameters may be calculated using different methods. For example, the first energy parameter may be the amplitude of the first peak frequency, whereas the second energy parameter may be the average amplitude of the frequencies within the second frequency band. Of course, any other suitable value could be used.

The first energy parameter E1 and the second energy parameter E2 determined by the vibration signal analysis unit 42 are output to a dryness determining unit 44. The dryness determining unit 44 takes the two energy parameters E1, E2 and accesses a database 46 in order to empirically determine the dryness of the steam. The database 46 contains a look-up table that contains reference or calibration data that correlates a range of first energy parameters E1 and second energy parameters E2 with steam dryness values. The reference or calibration data is data obtained by experimentation. The determining unit 44 determines the steam dryness value from the data in the look-up table and displays this dryness value on a local display 48. In addition to this, the dryness value is transmitted to a control room via a wireless connection using a wireless transmitter 50. This allows the steam dryness to be remotely monitored. In some embodiments the first energy parameter E1 may be converted to an actual flow velocity which is also output on the display. The flow velocity could be calculated or determined empirically from the first energy parameter E1. It should be appreciated that the look-up table may contain data that correlates a range of flow velocities and second energy parameters E2 with steam dryness values. As opposed to determining and outputting a dryness parameter, other parameters that express the phase compositions of the multiphase flow may be determined and output.

The dryness determining unit 44 is also configured to calculate the mass flow rate of the steam flow based on the steam dryness value and the flow velocity which may be determined from the first energy parameter E1. The mass flow rate may also be displayed on the display 48 and may also be transmitted using the transmitter 50.

The look-up table contained within the database 46 is created empirically. It may be necessary to create a new look-up table for each apparatus 10. However, it may be possible to produce a generic look-up table suitable for all apparatuses. In order to create the look-up table, a series of pre-determined volumes of water are injected into the steam line at range of flow velocities and for each combination of water volume/velocity the first energy parameter E1 and the second energy parameter E2 are recorded. The steam quality (or dryness) can be calculated from the known water volume and therefore by this calibration method a look-up table providing correlations between various first and second energy parameters E1, E2 can be created.

Although the peak frequencies of the target 38 remain substantially constant regardless of steam dryness, slight variations may occur in the peak frequencies if a film of water, for example, builds up on the face of the target 38. Further, a change in temperature of the target 38 may cause its mechanical properties to change which may also result in the peak frequencies shifting. It may be possible to determine the temperature of the steam from one or a combination of one or more peak frequencies.

In some arrangements it is possible that the first and second energy parameters E1, E2 are a function of the temperature, as well as of the flow velocity, and the dryness and flow velocity. If this is the case, a temperature sensor may be provided to measure the temperature of the steam. In such an arrangement the database 46 would contain a "three-dimensional" look-up table correlating first energy parameters E1 (or flow velocities), second energy parameters E2 and temperatures with dryness parameters. Instead of using a temperature sensor, it may be possible to use a pressure sensor and calculate (or estimate) the temperature from this, or the temperature (or pressure) may be determined from a peak frequency.

Although it has been described that the method and apparatus can be used for measuring the dryness of steam, it should be appreciated that the method and apparatus are also suitable for measuring the dryness of any other multiphase fluid flow.

What is claimed is:

1. A method, comprising:
   introducing a multiphase steam flow into a fluid line;
   mixing the steam flow upstream of a vibration sensor comprising a target disposed in the steam flow configured to vibrate in response to steam flow in the fluid line;
   obtaining a vibration signal in a time domain from the steam flow using the vibration sensor;
   analyzing the vibration signal including:
      transforming the vibration signal from a time domain to a frequency domain using a fast Fourier transform (FFT);
      determining a first energy parameter which is a total energy of the vibration signal within a predetermined first frequency band based on an oscillation amplitude of the vibration signal within the first frequency band, the first energy parameter being dependent on a flow velocity of the steam flow;
      determining a second energy parameter which is a total energy of the vibration signal within a predetermined second frequency band based on an oscillation amplitude of the vibration signal within the second frequency band, which second frequency band is at a higher frequency than the first frequency band, the second energy parameter being dependent on both the dryness of the steam flow and the flow velocity of the steam flow,
      wherein the total energy of the first frequency band and the second frequency band are each determined by summing the amplitudes of all frequencies within the respective frequency band;
   determining dryness of the steam flow by empirically determining a dryness parameter relating to the dryness of the steam flow using the first and second energy parameters; and
   outputting the dryness parameter by displaying and/or transmitting the dryness parameter.

2. A method of determining the dryness of a multiphase fluid flow in a fluid line, the method comprising: obtaining a vibration signal from the fluid flow using a vibration sensor comprising a target disposed in the fluid flow, wherein the target is configured to vibrate in response to the fluid flow in the fluid line; transforming the vibration signal from a time domain to a frequency domain using a fast Fourier transform (FFT), analyzing the vibration signal to determine a first energy parameter which is total energy determined by summing oscillation amplitudes of all frequencies within a predetermined first frequency band, and to determine a second energy parameter which is a total energy determined by summing oscillation amplitudes of all frequencies within a predetermined second frequency band; and determining a dryness parameter relating to the dryness of the multiphase fluid flow using the first and second energy parameters.

3. A method according to claim 2, further comprising mixing the fluid flow upstream of the vibration sensor.

4. A method according to claim 2, wherein the vibration sensor measures the vibration signal in a time domain.

5. A method according to claim 4, wherein analyzing the vibration signal includes transforming the vibration signal from the time domain to the frequency domain.

6. A method according to claim 2, wherein the first energy parameter is dependent on a flow velocity.

7. A method according to claim 2, wherein the second energy parameter is dependent on the phase compositions of the fluid flow and a flow velocity.

8. A method according to claim 2, wherein at least one of the first frequency band or the second frequency band is predetermined.

9. A method according to claim 2, wherein the first frequency band contains a first peak frequency and wherein the second frequency band contains a second peak frequency.

10. A method according to claim 2, wherein the first frequency band is at a lower frequency than the second frequency band.

11. A method according to claim 2, wherein determining a phase composition parameter comprises accessing a database containing data correlating first energy parameters and second energy parameters with phase composition parameters.

12. A method according to claim 2, further comprising outputting the phase composition parameter by transmitting the phase composition parameter.

13. An apparatus for determining the dryness of a multi-phase fluid flow flowing in a fluid line, comprising: a vibration sensor comprising a target configured such that when disposed in the fluid flow, it vibrates in response to fluid flow in the fluid line to obtain a vibration signal from the fluid flow; a vibration signal analysis unit configured to transform the vibration signal from a time domain to a frequency domain using a fast Fourier transform (FFT) and to analyze the vibration signal to determine a first energy parameter which is a total energy determined by summing oscillation amplitudes of all frequencies within a predetermined first frequency band, and a second energy parameter which is an a total energy determined by summing oscillation amplitudes of all frequencies within a predetermined second frequency band; and a phase composition determining unit configured to determine a phase composition parameter relating to the phase compositions of the fluid flow using the first and second energy parameters.

14. An apparatus according to claim 13, further comprising a fluid mixer configured to mix the fluid flow upstream of the vibration sensor.

15. An apparatus according to claim 13, wherein the vibration sensor further comprises an electrical converter configured to convert the vibration of the target into a vibration signal.

* * * * *